US009631244B2

(12) United States Patent
Foley et al.

(10) Patent No.: US 9,631,244 B2
(45) Date of Patent: Apr. 25, 2017

(54) REAGENT STORAGE ON A DROPLET ACTUATOR

(75) Inventors: Jennifer Foley, Cary, NC (US); Stefan Burde, Cary, NC (US); Vamsee K. Pamula, Cary, NC (US); Michael G. Pollack, Crumpler, NC (US)

(73) Assignee: ADVANCED LIQUID LOGIC, INC., San Diego, CA (US)

( * ) Notice: Subject to any disclaimer, the term of this patent is extended or adjusted under 35 U.S.C. 154(b) by 228 days.

(21) Appl. No.: 14/131,061

(22) PCT Filed: Jun. 26, 2012

(86) PCT No.: PCT/US2012/044235
§ 371 (c)(1),
(2), (4) Date: Jan. 6, 2014

(87) PCT Pub. No.: WO2013/006312
PCT Pub. Date: Jan. 10, 2013

(65) Prior Publication Data
US 2014/0141409 A1    May 22, 2014

Related U.S. Application Data

(63) Continuation-in-part of application No. 12/681,879, filed as application No. PCT/US2008/079812 on Oct. 14, 2008, now Pat. No. 8,460,528.

(60) Provisional application No. 61/504,793, filed on Jul. 6, 2011, provisional application No. 61/507,863, filed on Jul. 14, 2011, provisional application No. 60/980,622, filed on Oct. 17, 2007.

(51) Int. Cl.
| | | |
|---|---|---|
| *A61K 39/00* | (2006.01) | |
| *A61K 9/14* | (2006.01) | |
| *A61K 38/20* | (2006.01) | |
| *A61K 38/21* | (2006.01) | |
| *A61K 39/39* | (2006.01) | |
| *C12Q 1/70* | (2006.01) | |
| *B01L 3/00* | (2006.01) | |
| *B01L 7/00* | (2006.01) | |
| *C12Q 1/68* | (2006.01) | |

(52) U.S. Cl.
CPC ........ *C12Q 1/703* (2013.01); *B01L 3/502784* (2013.01); *B01L 3/502792* (2013.01); *B01L 7/525* (2013.01); *C12Q 1/6806* (2013.01); *B01L 2200/0678* (2013.01); *B01L 2200/16* (2013.01); *B01L 2300/0816* (2013.01); *B01L 2400/0427* (2013.01)

(58) Field of Classification Search
CPC ............ C12Q 1/6806; C12Q 2523/308; C12Q 2527/125; C12Q 2531/113; B01L 3/502792
See application file for complete search history.

(56) References Cited

U.S. PATENT DOCUMENTS

| | | |
|---|---|---|
| 4,127,460 A | 11/1978 | Gaske et al. |
| 4,244,693 A | 1/1981 | Guon |
| 4,636,785 A | 1/1987 | Le Pesant |
| 5,038,852 A | 8/1991 | Johnson et al. |
| 5,176,203 A | 1/1993 | Larzul |
| 5,181,016 A | 1/1993 | Lee et al. |
| 5,225,332 A | 7/1993 | Weaver et al. |
| 5,245,734 A | 9/1993 | Issartel |
| 5,266,498 A | 11/1993 | Tarcha et al. |
| 5,455,008 A | 10/1995 | Earley et al. |
| 5,472,881 A | 12/1995 | Beebe et al. |
| 5,486,337 A | 1/1996 | Ohkawa et al. |
| 5,498,392 A | 3/1996 | Wilding et al. |
| 5,720,923 A | 2/1998 | Haff et al. |
| 5,779,977 A | 7/1998 | Haff et al. |
| 5,817,526 A | 10/1998 | Kinoshita et al. |
| 5,827,480 A | 10/1998 | Haff et al. |
| 5,935,858 A | 8/1999 | Herst |
| 5,945,281 A | 8/1999 | Prabhu et al. |
| 5,998,224 A | 12/1999 | Rohr et al. |
| 6,013,531 A | 1/2000 | Wang et al. |
| 6,033,880 A | 3/2000 | Haff et al. |
| 6,063,339 A | 5/2000 | Tisone et al. |
| 6,130,098 A | 10/2000 | Handique et al. |

(Continued)

FOREIGN PATENT DOCUMENTS

| | | |
|---|---|---|
| JP | 2003112031 | 4/2003 |
| JP | 2006078225 A | 3/2006 |

(Continued)

OTHER PUBLICATIONS

Sigma, Product information, http://www.sigmaaldrich.com/content/dam/sigma-aldrich/docs/Sigma/Product_Information_Sheet/2/I8629pis.pdf, date created—2003: pdf pp. 1-4.*
Benton et al., "Library Preparation Method 1 DNA Library Construction for Illumine SBS Sequencing Platforms using NEBNext® Library Preparation Reagents", Application Note, NuGEN, 2011.
Boles et al., "Droplet-Based Pyrosequencing Using Digital Microfluidics", Analytical Chemistry, vol. 83, Sep. 2011, 8439-47.
Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.
Burde et al., "Digital Microfluidic Rapid HIV Point-of-Care Diagnostic Device for Resource Limited Settings", Workshop on TB and HIV Diagnostics, Silver Spring, MD. (Poster, copies distributed to attendees.) http://www.blsmeetings.net/TB-HIV-Dx-Wkshop/index.cfm, Jun. 28, 2011.

(Continued)

*Primary Examiner* — Janet L Andres
*Assistant Examiner* — Barry A Chestnut
(74) *Attorney, Agent, or Firm* — Dean D. Small; The Small Patent Law Group, LLC

(57) ABSTRACT

A method of providing a droplet comprising one or more reagents, the method comprising, depositing a first aqueous droplet comprising the one or more reagents on a surface; drying the droplet to yield a dried composition on the surface comprising the one or more reagents; covering the dried composition with oil; and causing a second aqueous droplet in the oil to contact the dried composition and thereby resuspend one or more reagents.

44 Claims, 4 Drawing Sheets

(56) References Cited

U.S. PATENT DOCUMENTS

| | | |
|---|---|---|
| 6,152,181 A | 11/2000 | Wapner et al. |
| 6,180,372 B1 | 1/2001 | Franzen |
| 6,294,063 B1 | 9/2001 | Becker et al. |
| 6,319,668 B1 | 11/2001 | Nova et al. |
| 6,453,928 B1 | 9/2002 | Kaplan et al. |
| 6,461,570 B2 | 10/2002 | Ishihara et al. |
| 6,548,311 B1 | 4/2003 | Knoll |
| 6,565,727 B1 | 5/2003 | Shenderov |
| 6,632,655 B1 | 10/2003 | Mehta et al. |
| 6,673,533 B1 | 1/2004 | Wohlstadter et al. |
| 6,734,436 B2 | 5/2004 | Faris et al. |
| 6,773,566 B2 | 8/2004 | Shenderov |
| 6,790,011 B1 | 9/2004 | Le Pesant et al. |
| 6,841,128 B2 | 1/2005 | Kambara et al. |
| 6,846,638 B2 | 1/2005 | Shipwash |
| 6,911,132 B2 | 6/2005 | Pamula et al. |
| 6,924,792 B1 | 8/2005 | Jessop |
| 6,955,881 B2 | 10/2005 | Tanaami |
| 6,977,033 B2 | 12/2005 | Becker et al. |
| 6,989,234 B2 | 1/2006 | Kolar et al. |
| 6,995,024 B2 | 2/2006 | Smith et al. |
| 7,052,244 B2 | 5/2006 | Fouillet et al. |
| 7,163,612 B2 | 1/2007 | Sterling et al. |
| 7,211,223 B2 | 5/2007 | Fouillet et al. |
| 7,211,442 B2 | 5/2007 | Gilbert et |
| 7,255,780 B2 | 8/2007 | Shenderov |
| 7,267,752 B2 | 9/2007 | King et al. |
| 7,328,979 B2 | 2/2008 | Decre et al. |
| 7,329,545 B2 | 2/2008 | Pamula et al. |
| 7,438,860 B2 | 10/2008 | Takagi et al. |
| 7,439,014 B2 | 10/2008 | Pamula et al. |
| 7,458,661 B2 | 12/2008 | Kim et al. |
| 7,495,031 B2 | 2/2009 | Sakuma et al. |
| 7,531,072 B2 | 5/2009 | Roux et al. |
| 7,547,380 B2 | 6/2009 | Velev |
| 7,556,776 B2 | 7/2009 | Fraden et al. |
| 7,569,129 B2 | 8/2009 | Pamula et al. |
| 7,579,172 B2 | 8/2009 | Cho et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,767,147 B2 | 8/2010 | Adachi et al. |
| 7,767,435 B2 | 8/2010 | Chiu et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,179,216 B2 | 5/2012 | Knospe |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,292,798 B2 | 10/2012 | Califorrniaa |
| 8,304,253 B2 | 11/2012 | Yi et al. |
| 8,313,698 B2 | 11/2012 | Pollack et al. |
| 8,317,990 B2 | 11/2012 | Pamula et al. |
| 8,337,778 B2 | 12/2012 | Stone et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0001544 A1 | 1/2002 | Hess et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0046948 A1 | 4/2002 | Chow et al. |
| 2002/0058332 A1 | 5/2002 | Quake et al. |
| 2002/0143437 A1 | 10/2002 | Handique et al. |
| 2003/0006140 A1 | 1/2003 | Vacca et al. |
| 2003/0007898 A1 | 1/2003 | Bohm et al. |
| 2003/0049177 A1 | 3/2003 | Smith et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0031688 A1 | 2/2004 | Shenderov |
| 2004/0055871 A1 | 3/2004 | Walton et al. |
| 2004/0055891 A1 | 3/2004 | Pamula et al. |
| 2004/0058450 A1 | 3/2004 | Pamula et al. |
| 2004/0086870 A1 | 5/2004 | Tyvoll et al. |
| 2004/0101445 A1 | 5/2004 | Shvets et al. |
| 2004/0161788 A1 | 8/2004 | Chen et al. |
| 2004/0180346 A1 | 9/2004 | Anderson et al. |
| 2004/0209376 A1 | 10/2004 | Natan et al. |
| 2004/0231987 A1 | 11/2004 | Sterling et al. |
| 2005/0056713 A1 | 3/2005 | Tisone et al. |
| 2005/0189049 A1 | 9/2005 | Ohno et al. |
| 2005/0227349 A1 | 10/2005 | Kim et al. |
| 2005/0237699 A1 | 10/2005 | Carroll |
| 2005/0282224 A1 | 12/2005 | Fouillet et al. |
| 2006/0021875 A1 | 2/2006 | Griffith et al. |
| 2006/0039823 A1 | 2/2006 | Yamakawa et al. |
| 2006/0040375 A1 | 2/2006 | Arney et al. |
| 2006/0054503 A1 | 3/2006 | Pamula et al. |
| 2006/0102477 A1 | 5/2006 | Vann et al. |
| 2006/0164490 A1 | 7/2006 | Kim et al. |
| 2006/0194331 A1 | 8/2006 | Pamula et al. |
| 2006/0210443 A1 | 9/2006 | Stearns et al. |
| 2006/0231398 A1 | 10/2006 | Sarrut et al. |
| 2006/0254933 A1 | 11/2006 | Adachi et al. |
| 2007/0023292 A1 | 2/2007 | Kim et al. |
| 2007/0037294 A1 | 2/2007 | Pamula et al. |
| 2007/0039866 A1 | 2/2007 | Schroeder et al. |
| 2007/0045117 A1 | 3/2007 | Pamula et al. |
| 2007/0064990 A1 | 3/2007 | Roth |
| 2007/0075922 A1 | 4/2007 | Jessop |
| 2007/0086927 A1 | 4/2007 | Natarajan et al. |
| 2007/0117959 A1 | 5/2007 | Shastri et al. |
| 2007/0179641 A1 | 8/2007 | Lucas et al. |
| 2007/0202538 A1 | 8/2007 | Glezer et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0003142 A1 | 1/2008 | Link et al. |
| 2008/0003588 A1 | 1/2008 | Hasson et al. |
| 2008/0006535 A1 | 1/2008 | Paik et al. |
| 2008/0023330 A1 | 1/2008 | Viovy |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0098917 A1 | 5/2008 | Rikihisa et al. |

(56) References Cited

U.S. PATENT DOCUMENTS

| | | |
|---|---|---|
| 2008/0105549 A1 | 5/2008 | Pamela et al. |
| 2008/0113081 A1 | 5/2008 | Hossainy et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0156983 A1 | 7/2008 | Fourrier et al. |
| 2008/0166793 A1 | 7/2008 | Beer et al. |
| 2008/0185296 A1 | 8/2008 | Sauter-Starace et al. |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0053726 A1 | 2/2009 | Owen et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1* | 11/2010 | Pollack et al. ............... 204/450 |
| 2010/0291578 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |
| 2013/0217113 A1 | 8/2013 | Srinivasan et al. |
| 2013/0217583 A1 | 8/2013 | Link et al. |
| 2013/0280131 A1 | 10/2013 | Handique et al. |

FOREIGN PATENT DOCUMENTS

| | | |
|---|---|---|
| JP | 2006329899 A | 12/2006 |
| JP | 2006329904 A | 12/2006 |
| JP | 2008096590 A | 4/2008 |
| WO | 0069565 A1 | 11/2000 |
| WO | 0073655 A1 | 12/2000 |
| WO | 2004011938 A2 | 2/2004 |
| WO | 2004029585 A1 | 4/2004 |
| WO | 2004030820 | 4/2004 |
| WO | 2004073863 A2 | 9/2004 |
| WO | 2005047696 A1 | 5/2005 |
| WO | 2005069015 A1 | 7/2005 |
| WO | 2006003292 A1 | 1/2006 |
| WO | 2006013303 A1 | 2/2006 |
| WO | 2006056787 A1 | 6/2006 |
| WO | 2006070162 A1 | 7/2006 |
| WO | 2006081558 | 8/2006 |
| WO | 2006085905 A1 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | WO2008098236 * | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |

(56) References Cited

FOREIGN PATENT DOCUMENTS

| | | | |
|---|---|---|---|
| WO | 2009052321 A2 | 4/2009 | |
| WO | 2009052345 A1 | 4/2009 | |
| WO | 2009052348 A2 | 4/2009 | |
| WO | 2009076414 | 6/2009 | |
| WO | 2009086403 A2 | 7/2009 | |
| WO | 2009111769 A2 | 9/2009 | |
| WO | 2009135205 A2 | 11/2009 | |
| WO | 2009137415 A2 | 11/2009 | |
| WO | 2009140373 A2 | 11/2009 | |
| WO | 2009140671 A2 | 11/2009 | |
| WO | 2010004014 A1 | 1/2010 | |
| WO | 2010006166 A2 | 1/2010 | |
| WO | 2010009463 A2 | 1/2010 | |
| WO | 2010019782 A2 | 2/2010 | |
| WO | 2010027894 A2 | 3/2010 | |
| WO | 2010042637 A2 | 4/2010 | |
| WO | 2010077859 A3 | 7/2010 | |
| WO | WO2010141921 | * | 12/2010 |
| WO | 2011002957 A2 | 1/2011 | |
| WO | 2011020011 A2 | 2/2011 | |
| WO | 2011057197 A2 | 5/2011 | |
| WO | 2011084703 A2 | 7/2011 | |
| WO | 2011126892 A2 | 10/2011 | |
| WO | 2012009320 A2 | 1/2012 | |
| WO | 2012012090 A2 | 1/2012 | |
| WO | 2012037308 A2 | 3/2012 | |
| WO | 2012068055 A3 | 5/2012 | |
| WO | 2013009927 A3 | 1/2013 | |

OTHER PUBLICATIONS

Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems, 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36

Cohen, "Automated Multianalyte Screening Tool for Classification of Forensic Samples", NIJ conference 2012, http://www.nij.gov/nij/events/nij_conference/2012/nij-2012-program-book.pdf, 2012, Cohen, "Digital Microfluidic Sample Prep & Bioanalytical Systems", BioDot Workshop: From R&D to Quantitative IVDs, Irvine, CA, Apr. 24, 2012.

Cotten et al., "Digital Microfluidics: a novel platform for multiplexed detection of lysosomal storage diseases", Abstract # 3747.9. Pediatric Academic Society Conference.

Delapierre et al., "SmartDrop: An Integrated System from Sample Collection to Result using real-time PCR," 4th National Bio-Threat Conference, Dec. 7-9, 2010, New Orleans, LA, USA; Abstract in Proceedings, Poster presented at conference.

Delattre, Movie in news on TF1 (at 12'45" Cyril Delattre), http://videos.tf1.fr/jt-we/zoom-sur-grenoble-6071525.html, 2009.

Delattre, Movie in talk show "C Dans l'air" (at 24" Cyril Delattre), http://www.france5.fr/c-dans-l-air/sante/bientot-vous-ne-serez-plus-malade-31721, 2009.

Delattre, Movie on Web TV—Cite des sciences (at 3'26" Cyril Delattre), http://www.universcience.tv/video-laboratoire-de-poche-793.html, 2009.

Delattre et al., "Macro to microfluidics system for biological environmental monitoring", Biosensors and Bioelectronics, vol. 36, Issue 1, 2012, Available online, Apr. 27, 2012, 230-235.

Delattre et al., "SmartDrop: an integrated system from sample preparation to analysis using real-time PCR", 10th International Symposium on Protection against Chemical and Biological Warfare Agents; Stockholm, Sweden; poster, Jun. 10, 2010.

Delattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.

Delattre et al., "Towards an industrial fabrication process for electrowetting chip using standards MEMS Technology", μTAS2008, San Diego; poster presented, Oct. 15, 2008.

Delattre et al., "Towards an industrial fabrication process for electrowetting chip using standard MEMS Technology", μTAS2008, San Diego; Abstract in proceedings, Oct. 13-16, 2008, 1696-1698.

Dewey, "Towards a Visual Modeling Approach to Designing Microelectromechanical System Transducers", Journal of Micromechanics and Microengineering, vol. 9, Dec. 1999, 332-340.

Dewey et al., "Visual modeling and design of microelectromechanical system tansducers", Microelectronics Journal, vol. 32, Apr. 2001, 373-381.

Eckhardt et al., "Development and validation of a single-step fluorometric assay for Hunter syndrome", APHL Newborn Screening and Genetic Testing Symposium, San Diego, 2011.

Emani et al., "Novel microfluidic platform for automated lab-on-chip testing of hypercoagulability panel", Blood Coagulation and Fibrinolysis, vol. 23(8), 2012, 760-8.

Emani et al., "Novel Microfluidic Platform for Point of Care Hypercoagulability Panel Testing", Circulation, vol. 122, 2010, A14693.

Fair et al., "A Micro-Watt Metal-Insulator-Solution-Transport (MIST) Device for Scalable Digital Bio-Microfluidic Systems", IEEE IEDM Technical Digest, 2001, 16.4. 1-4.

Fair et al., "Advanced in droplet-based bio lab-on-achip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

Fair et al., "Chemical and biological pathogen detection in a digital microfluidic platform", DARPA Workshop on Microfluidic Analyzers for DoD and National Security Applications, Keystone, CO, 2006.

Fair, "Digital microfluidics: is a true lab-on-a-chip possible?", Microfluid Nanofluid, vol. 3, Mar. 8, 2007, 245-281.

Fair, "Droplet-based microfluidic Genome sequencing", NHGRI PI's meeting, Boston.

Fair et al., "Electrowetting-based On-Chip Sample Processing for Integrated Microfluidics", IEEE Inter. Electron Devices Meeting (IEDM), 2003, 32.5.1-32.5.4.

Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.

Fair, "Scaling of Digital Microfluidic Devices for Picoliter Applications", The 6th International Electrowetting Meeting, Aug. 20-22, 2008, p. 14.

(56) References Cited

OTHER PUBLICATIONS

Fouillet, "Bio-Protocol Integration in Digital Microfluidic Chips", The 6th International Electrowetting Meeting, Aug. 20-22, 2008, p. 15.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet et al., "Digital microfluidic design and optimization of classic and new fluidic functions for lab on a chip systems", Microfluid Nanofluid, vol. 4, 2008, 159-165.

Graham et al., "Development of Quality Control Spots for Lysosomal Storage Disorders under cGMP", APHL Newborn Screening and Genetic Testing Symposium, San Diego, 2011.

Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.

Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. µTAS, Oct. 12-16, 2008.

Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.

Jary et al., "SmartDrop, Microfluidics for Biology", Forum 4i 2009, Grenoble, France; Flyer distributed at booth, May 14, 2009.

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99/3800, 30th AIAA Fluid Dynamics Conference, Norfolk, VA, (Invited lecture), Jun. 1999, pp. 1-6.

Kleinert et al., "Dynamics and Stability of Oil Films During Droplet Transport by Electrowetting", 86th ACS Colloid & Surface Science Symposium, Abstract, Jun. 13, 2012.

Kleinert et al., "Dynamics and Stability of Oil Films During Droplet Transport by Electrowetting", 86th ACS Colloid & Surface Science Symposium, Presentation, Jun. 13, 2012.

Kleinert et al., "Dynamics and stability of oil films during droplet transport by electrowetting", 8th International Meeting on Electrowetting, Athens, Greece, Jun. 21-23, 2012.

Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.

Kleinert, "Electric-Field-Assisted Convective Assembly of Colloidal Crystal Coatings", May 13, 2010, 10380-10385.

Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.

Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal&id=ASMECP002010054501000239000000, Aug. 1-5, 2010.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

Millington et al., "Applications of tandem mass spectrometry and microfluidics in newborn screening", Southeastern Regional Meeting of the American Chemical Society, Raleigh, North Carolina, 2012.

Millington et al., "Digital microfluidics: a future technology in the newborn screening laboratory", Seminars in Perinatology, vol. 34, Apr. 2010, 163-169.

Millington et al., "Digital Microfluidics: a novel platform for multiplexed detection of LSDs with potential for newborn screening", Association of Public Health Laboratories Annual Conference, San Antonio, TX, Nov. 4, 2008.

Millington et al., "Digital Microfluidics: A Novel Platform for Multiplexing Assays Used in Newborn Screening", Proceedings of the 7th International and Latin American Congress. Oral Presentations. Rev Invest Clin; vol. 61 (Supl. 1), 2009, 21-33.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; POSTER, 2005.

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", 11th International Conference on Miniaturized Systems for Chemistry and Life Sciences, Oct. 7-11, 2007, 1559-1561.

Paik et al., "Programmable flow-through real-time PCR using digital microfluidics", Proc. Micro Total Analysis Systems (µTAS), Handout, 2007.

Paik et al., "Programmable flow-through real-time PCR using digital microfluidics", Proc. Micro Total Analysis Systems (µTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

(56) References Cited

OTHER PUBLICATIONS

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula, "Digital microfluidic lab-on-a-chip for multiplexing tests in newborn screening", Newborn Screening Summit: Envisioning a Future for Newborn Screening, Bethesda, MD, Dec. 7, 2009.
Pamula et al., "Digital microfluidic lab-on-a-chip for protein crystallization", 5th Protein Structure Initiative "Bottleneck" Workshop, NIH, Bethesda, MD, Apr. 13-14, 2006, I-16.
Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.
Pamula et al., "Digital Microfluidic Platform for Multiplexing LSD Assays in Newborn Screening", LSD WORLD Meeting, Las Vegas, NV, Feb. 16-18, 2011.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula et al., "Rapid LSD assays on a multiplex digital microfluidic platform for newborn screening", Lysosomal Disease Network World Symposium 2012, San Diego, CA, Feb. 8-19, 2012, 39.
Pamula, "Sample Preparation and Processing using Magnetic Beads on a Digital Microfluidic Platform", CHI's Genomic Sample Prep, San Francisco, CA, Jun. 9-10, 2009.
Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.
Pollack et al., "Applications of Electrowetting-Based Digital Microfluidics in Clinical Diagnostics", Expert Rev. Mol. Diagn., vol. 11(4), 2011, 393-407.
Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Pollack, "Sample Preparation Using Digital Microfluidics", Sample Prep 2012, Knowledge Press, Inc., May 3-4, 2012.
Punnamaraju, "Voltage and Photo Induced Effects in Droplet-Interface-Bilayer Lipid", PhD Thesis, University of Cincinnati, 2011.
Punnamaraju et al., "Voltage Control of Droplet Interface Bilayer Lipid Membrane Dimensions", Langmuir The ACS Journal of Surfaces and Colloids, vol. 27, Issue 2, 2011, Published on Web, Dec. 10, 2010, 618-626.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.
Rival et al., "Expression de gènes de quelques cellules sur puce EWOD/Gene expression of few cells on EWOD chip", iRTSV,http://www-dsv.cea.fr/var/plain/storage/original/media/File/iRTSV/thema_08(2).pdf (english translation), Winter 2009-2010.
Rival et al., "New insight on droplet dynamics under electrowetting actuation and design tools for speeding up product development", 8th Electrowetting Workshop, Athens, Greece. Abstract, 2012.
Rival et al., "New insight on droplet dynamics under electrowetting actuation and design tools for speeding up product development", 8th Electrowetting Workshop, Athens, Greece, Presentation, 2012.
Rival et al., "Towards Single Cells Gene Expression on EWOD Lab on Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Nanobio Europe 2009, Abstract in proceedings, Jun. 16-18, 2009.
Rival et al., "Towards single cells gene expression preparation and analysis on ewod lab on chip", Lab on Chip Europe 2009 poster distributed at Conference, May 19-20, 2009.
Rival et al., "Towards single cells gene expression preparation and analysis on ewod lab on chip", Lab on Chip Europe 2009, Abstract in proceedings, May 19-20, 2009.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Sandahl et al., "Automated Multianalyte Screening for Classification of Forensic Samples", 23rd International Symposium for Human Identification, Nashville, TN. http://www.promega.com/~/media/files/resources/conference%20proceedings/ishi%2023/poster%20abstracts/31%20poster.pdf?la=en, Oct. 16-17, 2012.
Schell et al., "Evaluation of a Digital Microfluidic real-time PCR Platform to detect DNA of Candida albicans", Eur. J. Clin Microbiol Infect Dis, Published on-line DOI 10.1007/s10096-012-15616, Feb. 2012.

(56) References Cited

OTHER PUBLICATIONS

Sherman et al., "Flow Control by Using High-Aspect-Ratio, In-Plane Microactuators", 1999, pp. 169-175.

Sherman et al., "In-Plane Microactuator for Fluid Control Application", Proc. IEEE Micro Electro Mechanical Systems Workshop, Heidelberg, Germany, Jan. 1998, pp. 454-459.

Shi et al., "Evaluation of stability of fluorometric reagent kits for screening of Lysosomal Storage Disorders", APHL Newborn Screening and Genetic Testing Symposium, San Diego, 2011.

Sista et al., "96-Immunoassay Digital Microfluidic Multiwell Plate", Proc. μTAS, Oct. 12-16, 2008.

Sista, "Development of a Digital Microfluidic Lab-on-a-Chip for Automated Immunoassays with Magnetically Responsive Beads", PhD Thesis, Department of Chemical Engineering, Florida State University, 2007.

Sista et al., "Development of a digital microfluidic platform for point of care testing", Lab on a chip, vol. 8, Dec. 2008, First published as an Advance Article on the web, Nov. 5, 2008, 2091-2104.

Sista et al., "Digital Microfluidic Platform for Multiplexing Enzyme Assays: Implications for Lysosomal Storage Disease Screening in Newborns", Clinical Chemistry, vol. 57, Aug. 22, 2011, 1444-51.

Sista et al., "Digital Microfluidic platform for multiplexing LSD assays in newborn screening", APHL Newborn Screening and Genetic Testing Symposium, Orlando, May 3-6, 2010.

Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.

Sista et al., "Multiplex Digital Microfluidic Platform for Rapid Newborn Screening of Lysosomal Storage Disorders", ACMG Annual Meeting, Charlotte, NC, 2012.

Sista et al., "Performance of a digital microfluidic assay for Gaucher and Hurler disorders", APHL Newborn Screening and Genetic Testing Symposium, San Diego, 2011.

Sista et al., "Rapid, Single-Step Assay for Hunter Syndrome in Dried Blood Spots Using Digital Microfluidics", Clinica Chimica Acta, vol. 412, 2011, 1895-97.

Sista et al., "Spatial multiplexing of immunoassays for small-volume samples", 10th PI Meeting IMAT, Bethesda, 2009.

Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.

Srinivasan et al., "A digital microfluidic biosensor for multianalyte detection", Proc. IEEE 16th Annual Int'l Conf. on Micro Electro Mechanical Systems Conference, 2003, 327-330.

Srinivasan, "A Digital Microfluidic Lab-on-a-Chip for Clinical Diagnostic Applications", Ph.D. thesis, Dept of Electrical and Computer Engineering, Duke University, 2005.

Srinivasan et al., "An integrated digital microfluidic lab-on-a-chip for clinical diagnostics on human physiological fluids", Lab on a Chip, vol. 4, 2004, 310-315.

Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.

Srinivasan et al., "Commercializing electrowetting-based digital microfluidics: from the lab to a product", 8th International Meeting on Electrowetting, Athens, Greece, Jun. 21-23, 2012.

Srinivasan et al., "Digital Microfluidic Lab-on-a-Chip for Protein Crystallization", The 82nd ACS Colloid and Surface Science Symposium, 2008.

Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.

Srinivasan et al., "Droplet-based microfluidic lab-on-a-chip for glucose detection", Analytica Chimica Acta, vol. 507, No. 1, 2004, 145-150.

Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.

Srinivasan et al., "Feasibility of a point of care newborn screening platform for hyperbilirubinemia", APHL Newborn Screening and Genetic Testing Symposium, San Diego, 2011.

Srinivasan et al., "Low cost digital microfluidic platform for protein crystallization", Enabling Technologies for Structural Biology, NIGMS Workshop, Bethesda, MD., Mar. 4-6, 2009, J-23.

Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.

Srinivasan et al., "Scalable Macromodels for Microelectromechanical Systems", Technical Proc. 2001 Int. Conf. on Modeling and Simulation of Microsystems, 2001, 72-75.

Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.

Sudarsan et al., "Printed circuit technology for fabrication of plastic based microfluidic devices", Analytical Chemistry vol. 76, No. 11, Jun. 1, 2004, Previously published on-line, May 2004, 3229-3235.

Thwar et al., "DNA sequencing using digital microfluidics", Poster 42, 41st AACC's. Annual Oak Ridge Conference Abstracts, Clinical Chemistry vol. 55, 2009, 1891.

Tolun et al., "A Novel Fluorometric Enzyme Analysis Method for Hunter Syndrome Using Dried Blood Spots", Mol. Genet. Metab., 105, Issue 3, 2012; doi:10.1016/j.ymgme.2011.12.011, Epub, Dec. 21, 2011, 519-521.

Tolun et al., "Dried blood spot based enzyme assays for lysosomal storage disorders", 2011 Tokyo Meeting on Lysosomal Storage Disease Screening, Tokyo, Aug. 5, 2011.

Wang et al., "Comparison of enzyme activities for Pompe, Fabry, and Gaucher diseases on CDC's Quality Control spots between microplate fluorometry, mass spectrometry, and digital microfluidic fluorometry", APHL Newborn Screening and Genetic Testing Symposium, San Diego, 2011.

Wang et al., "Droplet-based micro oscillating-flow PCR chip", J. Micromechanics and Microengineering, vol. 15, 2005, 1369-1377.

Wang et al., "Efficient in-droplet separation of magnetic particles for digital microfluidics", Journal of Micromechanics and Microengineering, vol. 17, 2007, 2148-2156.

Weaver, "Application of Magnetic Microspheres for Pyrosequencing on a Digital Microfluidic Platform", Department of Electrical and Computer Engineering, Duke University, 2005.

Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.

Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.

Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Defect-Tolerant Design and Optimization of a Digital Microfluidic Biochip for Protein Crystallization", IEEE Transactions on Computer Aided Design, vol. 29, No. 4, 2010, 552-565.

(56) References Cited

OTHER PUBLICATIONS

Xu et al., "Design and Optimization of a Digital Microfluidic Biochip for Protein Crystallization", Proc. IEEE/ACM International Conference on Computer-Aided Design (ICCAD), Nov. 2008, 297-301.
Xu et al., "Digital Microfluidic Biochip Design for Protein Crystallization", IEEE-NIH Life Science Systems and Applications Workshop, LISA, Bethesda, MD, Nov. 8-9, 2007, 140-143.
Xu et al., "Droplet-Trace-Based Array Partitioning and a Pin Assignment Algorithm for the Automated Design of Digital Microfluidic Biochips", CODES, 2006, 112-117.
Xu et al., "Integrated Droplet Routing in the Synthesis of Microfluidic Biochips", IEEE, 2007, 948-953.
Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Yang et al., "Manipulation of droplets in microfluidic systems", Trends in Analytical Chemistry, vol. 29, Feb. 2010, 141-157.
Yao et al., "Spot Cooling Using Thermoelectric Microcooler", Proc. 18th Int. Thermoelectric Conf, Baltimore, VA, pp. 256-259, Aug. 1999.
Yi et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi et al., "Characterization of electrowetting actuation on addressable single-side coplanar electrodes", Journal of Micromechanics and Microengineering, vol. 16.,Oct. 2006, 2053-2059.
Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.
Yi, "Soft Printing of Biological Liquids for Micro-arrays: Concept, Principle, Fabrication, and Demonstration", Ph.D. dissertation, UCLA, 2004.
Yi et al., "Soft Printing of Droplets Digitized by Electrowetting", Transducers 12th Int'l Conf. on Solid State Sensors, Actuators and Microsystems, Boston, Jun. 8-12, 2003.
Yi et al., "Soft Printing of Droplets Pre-Metered by Electrowetting", Sensors and Actuators A: Physical, vol. 114, Jan. 2004, 347-354.
Zeng et al., "Actuation and Control of Droplets by Using Electrowetting-on-Dielectric", Chin. Phys. Lett., vol. 21(9), 2004, 1851-1854.
Zhao et al., "Droplet Manipulation and Microparticle Sampling on Perforated Microfilter Sampling on Perforated Microfilter Membranes", J. Micromech. Microeng., Vol. 18, 2008, 1-11.
Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.
Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.
Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.
Zhao et al., "Optimization Techniques for the Synchronization of Concurrent Fluidic Operations in Pin-Constrained Digital Microfluidic Biochips", IEEE Transactions on Very Large Scale Integration (VLSI) Systems, vol. 20, No. 6, Jun. 2012, 1132-1145.
Zhao et al., "Synchronization of Concurrently-Implemented Fluidic Operations in Pin-Constrained Digital Microfluidic Biochips", VLSI Design, (Best Paper Award), 2010.
Lapierre et al. "High sensitive matrix-free mass spectrometry analysis of peptides using silicon nanowires-based digital microfluidic device", Lab on a Chip, vol. 11, No. 9, Mar. 31, 2011 (Mar. 31, 2011), p. 1620.
Wheeler et al. "Digital microfluidics with in-line sample purification for proteomics analyses with MALDI-MS", EPO Form 1703 01.91TRI Analytical chemistry, Jan. 15, 2005 (Jan. 15, 2005), pp. 534-540.
Malic et al. "Biochip functionalization using electrowetting-on-dielectric digital microfluidics for surface plasmon resonance imaging detection of DNA hybridization", Biosensors and Biolectronics, Elsevier BV, NL, vol. 24, No. 7, Mar. 15, 2009 (Mar. 15, 2009). pp. 2218-2224.
Jebrail et al. "Digital Microfluidic Method for Protein Extraction by Precipitation", Analytical Chemistry, American Chemical Society, US, vol. 81, No. 1, Dec. 13, 2008 (Dec. 13, 2008), pp. 330-335.
International Search Report dated Jan. 28, 20012 from PCT International Application No. PCT/US20012/044235.
European Search Report dated Feb. 6, 2015 from EP Application No. EP 12807397.0.
PCT International Preliminary Report on Patentability for PCT/US2012/044235 dated Jan. 7, 2014.
Abstract from National Institutes of Health Grant No. 1R01HG004354-01 titled "Continuous Sequencing-By-Synthesis Based on a Digital Microfluidic Platform" with a project start date of Aug. 1, 2007.
Sato et al. (Anal. Chem. 2000, 72, 1144-1147).
Office Action dated Sep. 7, 2012 from related U.S. Appl. No. 12/681,879.
International Preliminary Report on Patentability dated Apr. 20, 2010 from PCT International Application No. PCT/US2008/079812.
International Search Report dated Dec. 16, 2008 from PCT International Application No. PCT/US2008/079812.
Binks, "Wetting: theory and experiment", Current Opinion in Colloids and Interface Science, vol. 6, No. 1, Feb. 17-21, 2001.
Chamberlain, et al., "Deletion screening of Duchenne musular dystrophy locus via multiplex DNA amplification", Nuc. Acid. Res. 16, pp. 11141-11156, Aug. 24, 1988.
Cho, et al., "Concentration and binary separation of micro particles for droplet-based digital microfluidics", Lab Chip, vol. 7, 490-498, Feb. 12, 2007.
Coltro et al., "Toner and paper-based fabrication techniques for microfluidic applications", Electrophoresis, vol. 31, 2487-2498, Jul. 2010.
Dorfman, et al., "Contamination-Free Continuouse Flow Microfluidic Polymerase Chain Reaction for Quantitative and Clinical Applications", Analytical Chemistry 77, 3700-3704, Jun. 1, 2005.
Fowler, "Labon-on-a-Chip Technology May Present New ESD Challenges", Electrostatic Discharge (ESD) Journal. Retrieved on Apr. 18, 2008 from:http://www.esdjournal.com/articles/labchip/Lab.htm., Mar. 2002.
Gijs, Mam, "Magnetic bead handling on-chip:new opportunities for analytical applications", Microfluidics and Nanofluidics, vol. 1, 22-40, Oct. 2, 2004.
Huang, et al., "MEMS-based sample preparation for molecular diagnostics", Analytical and Bioanalytical Chemistry, vol. 372, 49-65, Jan. 2002.
Jones, et al., "Dielectrophoretic liquid actuation and nanodroplet formation", J. Appl. Phys., vol. 89, No. 2, 1441-1448, Jan. 2001.
Kim, et al., "Electrowetting on paper for electronic paper display", ACS Applied Materials & Interfaces, vol. 2, 3318-3323, Nov. 2010.
Margulies, et al., "Genome sequencing in microfabricated high-density picolitre reactors", Nature, vol. 437, 376-380 and Supplemental Materials, Sep. 2005.
Pamula et al., "Digital Microfluidics for Lab-on-a-Chip Applications", "Emerging CAD Challenges for Biochip Design" Workshop, Conference on Design, Automation, and Test in Europe (DATE), Munich, Germany, Advance Programme, pp. 85-87, Mar. 2006.

(56) References Cited

OTHER PUBLICATIONS

Park, et al., "Single-sided continuous optoelectrowetting (SCOEW) droplet manipulation with light patterns", Lab on a chip, vol. 10, 1655-1661, Jul. 2010.

Pinho, et al., "Haemopoietic progenitors in the adult mouse omentum: permanent production of B lymphocytes and monocytes", Cell Tissue Res., vol. 319, No. 1, 91-102, Jan. 2005.

Poliski, Making materials fit the future: accommodating relentless technological requirements means researchers must recreate and reconfigure materials, frequently challenging established laws of physics, while keeping an eye on Moore's Law, R&D Magazine Conference, Dec. 2001.

Raj, et al., Composite Dielectrics and Surfactants for Low Voltage Electrowetting Devices, University/Government/Industry Micro/Nano Symposium, vol. 17, 187-190, Jul. 13-16, 2008.

Russom, et al., "Pyrosequencing in a Microfluidic Flow-Through Device", Anal. Chem. vol. 77, 7505-7511, Nov. 2005.

Schwartz, et al., "Dielectrophoretic approaches to sample preparation and analysis", The University of Texas, Dissertation, Dec. 2001.

Shah, et al., "EWOD-driven droplet microfluidic device integrated with optoelectronic tweezers as an automated platform for cellular isolation and analysis", Lab on a Chip, vol. 9, 1732-1739, Jun. 2009.

Tsuchiya, et al., "On-chip polymerase chain reaction microdevice employing a magnetic droplet-manipulation system", Sensors and Actuators B, vol. 130, 583-588, Oct. 18, 2007.

Welch, et al., "Picoliter DNA sequencing chemistry on an electrowetting-based digital microfluidic platform", Biotechnology Journal, vol. 6, 165-176, Feb. 2011.

Wheeler, et al., "Electrowetting-Based Microfluidics for Analysis of Peptides and Proteins by Matrix-Assisted Laser Desportion/Ionization Mass Spectrometry", Anal. Chem. 76, 4833-4838, Jul. 2004.

Yi et al., "Microfluidics technology for manipulation and analysis of biological cells", Analytica Chimica Acta, vol. 560, Jan. 1-23, 2006.

* cited by examiner

REAGENT STORAGE ON A DROPLET ACTUATOR

1 GOVERNMENT INTEREST

This invention was made with government support under HG004354 awarded by the National Institutes of Health of the United States. The United States Government has certain rights in the invention.

2 BACKGROUND

A droplet actuator typically includes one or more substrates configured to form a surface or gap for conducting droplet operations. The one or more substrates establish a droplet operations surface or gap for conducting droplet operations and may also include electrodes arranged to conduct the droplet operations. The droplet operations substrate or the gap between the substrates may be coated or filled with a filler fluid that is immiscible with the liquid that forms the droplets.

Droplet actuators are used in a variety of applications, including molecular diagnostic testing, such as point-of-care testing in which the flexibility and breadth of digital microfluidics provide a rapid and sensitive multifunctional testing device. For point-of-care testing, diagnostic devices are typically provided pre-loaded with the required assay reagents for a diagnostic test. Consequently, there is a need for methods for storing assay reagents on a droplet actuator.

3 DEFINITIONS

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating or direct current. Any suitable voltage may be used. For example, an electrode may be activated using a voltage which is greater than about 150 V, or greater than about 200 V, or greater than about 250 V, or from about 275 V to about 375 V, or about 300 V. Where alternating current is used, any suitable frequency may be employed. For example, an electrode may be activated using alternating current having a frequency from about 1 Hz to about 100 Hz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a fluid path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication Nos. 20050260686, entitled "Multiplex flow assays preferably with magnetic particles as solid phase," published on Nov. 24, 2005; 20030132538, entitled "Encapsulation of discrete quanta of fluorescent particles," published on Jul. 17, 2003; 20050118574, entitled "Multiplexed Analysis of Clinical Specimens Apparatus and Method," published on Jun. 2, 2005; 20050277197. Entitled "Microparticles with Multiple Fluorescent Signals and Methods of Using Same," published on Dec. 15, 2005; 20060159962, entitled "Magnetic Microspheres for use in Fluorescence-based Applications," published on Jul. 20, 2006; the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/047486, entitled "Droplet-Based Biochemistry," filed on Dec. 11, 2006; Shenderov, U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000; Kim and/or Shah et al., U.S. patent application Ser. No. 10/343,261, entitled "Electrowetting-driven Micropumping," filed on Jan. 27, 2003, Ser. No. 11/275,668, entitled "Method and Apparatus for Promoting the Complete Transfer of Liquid Drops from a Nozzle," filed on Jan. 23, 2006, Ser. No. 11/460,188, entitled "Small Object Moving on Printed Circuit Board," filed on Jan. 23, 2006, Ser. No. 12/465,935, entitled "Method for Using Magnetic Particles in Droplet Microfluidics," filed on May 14, 2009, and Ser. No. 12/513,157, entitled "Method and Apparatus for Real-time Feedback Control of Electrical Manipulation of Droplets on Chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker and Gascoyne et al., U.S. Pat. No. 7,641,779, entitled "Method and Apparatus for Programmable fluidic Processing," issued on Jan. 5, 2010, and U.S. Pat. No. 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," Lab Chip, 10:832-836 (2010); the entire disclosures of which are incorporated herein by reference, along with their priority documents. Certain droplet actuators will include one or more substrates arranged with a gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the invention. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define dispensing reservoirs. The spacer height may, for example, be from about 5 µm to about 600 µm, or about 100 µm to about 400 µm, or about 200 µm to about 350 µm, or about 250 µm to about 300 µm, or about 275 µm. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the invention include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and opto-electrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the invention. Similarly, one or more of the foregoing may be used to deliver liquid into a droplet operations gap, e.g., from a reservoir in another device or from an external reservoir of the droplet actuator (e.g., a reservoir associated with a droplet actuator substrate and a fluid path from the reservoir into the droplet operations gap). Droplet operations surfaces of certain droplet actuators of the invention may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), and other fluorinated monomers for plasma-enhanced chemical vapor deposition (PECVD). In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Application No. PCT/US2010/040705, entitled "Droplet Actuator Devices and Methods," the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness in the range of about 20 to about 200 nm, preferably about 50 to about 150 nm, or about 75 to about 125 nm, or about 100 nm. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® non-woven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass) and PARYLENE™ N (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; and polypropylene. Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the invention may derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, and other fluorinated monomers for plasma-enhanced chemical vapor deposition (PECVD). Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the invention includes those described in Meathrel, et al., U.S. Pat. No. 7,727,466, entitled "Disintegratable films for diagnostic devices," granted on Jun. 1, 2010.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., International Patent Pub. No. WO/2008/101194, entitled "Capacitance Detection in a Droplet Actuator," published on Aug. 21, 2008, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×-3×-droplets are usefully controlled operated using 1, 2, and 3 electrodes, respectively. If the droplet footprint is greater than the number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the gap of a droplet actuator is typically filled with a filler fluid. The filler fluid may, for example, be a low-viscosity oil, such as silicone oil or hexadecane filler fluid. The filler fluid may fill the entire gap of the droplet actuator or may coat one or more surfaces of the droplet actuator. Filler fluids may be conductive or non-conductive. Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the invention are provided in Srinivasan et al, International Patent Pub. Nos. WO/2010/027894, entitled "Droplet Actuators, Modified Fluids and Methods," published on Mar. 11, 2010, and WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Aug. 14, 2008; and Monroe et al., U.S. Patent Publication No. 20080283414, entitled "Electrowetting Devices," filed on May 17, 2007; the entire disclosures of which are incorporated herein by reference, as well as the other patents and patent applications cited herein.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Reservoir" means an enclosure or partial enclosure configured for holding, storing, or supplying liquid. A droplet actuator system of the invention may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or fluid path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the invention, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

4 BRIEF DESCRIPTION OF THE DRAWINGS

Figure 3A:
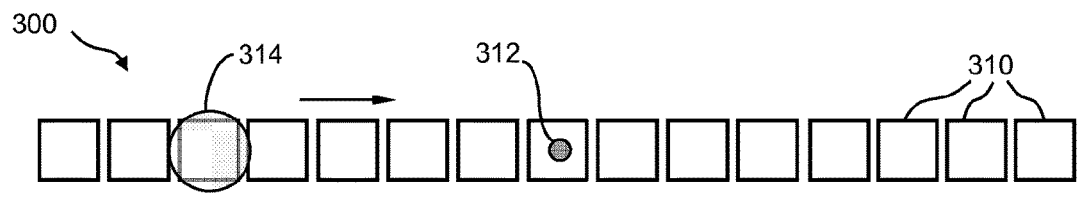
Figure 3B:
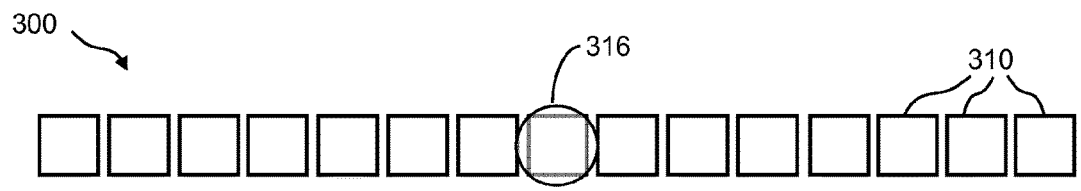
Figure 3C:
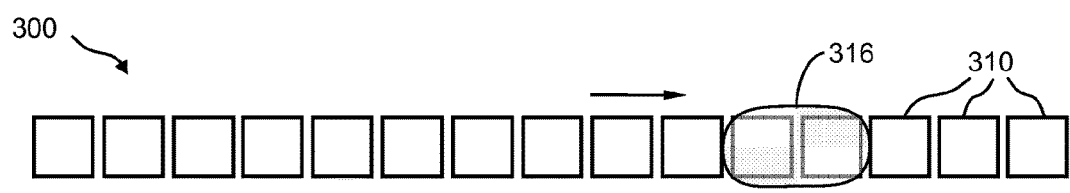

FIGS. 3A, 3B, and 3C illustrate top views of an example of a portion of an electrode arrangement of a droplet actuator and show a process of performing a reagent reconstitution protocol on a droplet actuator; and FIGS. 4A through 4E illustrate top views of the electrode arrangement of FIG. 3A and show another process of performing a reagent reconstitution protocol on a droplet actuator.

5 DESCRIPTION

The invention provides methods for storage and reconstitution (i.e., reagent recovery) of assay reagents on a droplet actuator. In one embodiment, the invention provides methods for drying one or more assay reagents on a solid surface of a droplet actuator. In another embodiment, the invention provides methods for storing one or more liquid reagents on a droplet actuator. In yet another embodiment, the invention provides methods for recovery of one or more dried assay reagents from a solid surface of a droplet actuator using digital microfluidic liquid handling protocols. The dried reagent and the surface may be covered with a filler fluid, such as a silicone oil.

Assay reagents may be preloaded and stored on a droplet actuator as dried reagents, liquid reagents, and/or any combination thereof. Storage format (i.e., dried reagent or liquid reagent) may be selected to provide maximum stability of stored reagents (e.g., shelf-life of 12 months or more). Storage format may be selected such that no special handling, precautions or storage conditions are required. User intervention is minimized because assay reagents are preloaded on a droplet actuator and digital microfluidic liquid handling protocols are used for reconstitution of dried reagent.

In one embodiment, the methods of the invention are used to provide a preloaded, disposable droplet actuator that is suitable for point-of-care (POC) and sample-to-answer diagnostic testing. In one example, the methods of the invention may be used for reagent storage and reconstitution on a droplet actuator configured for POC and sample-to-answer testing for HIV. In this example, dried reagents for sample preparation, immunoassays for antibodies to HIV, and reverse transcription quantitative PCR (RT-qPCR) for HIV viral load may be preloaded and stored on a droplet actuator. Liquid reagents, such as wash buffers and oil filler fluid, may also be stored on the droplet actuator.

5.1 Reagent Storage on a Droplet Actuator

The invention provides methods for reagent storage and reconstitution (i.e., reagent recovery) on a droplet actuator. Available reagent drying technologies for preserving and storing chemical reagents (e.g., sample preparation reagents, immunoassay reagents, and RT-qPCR reagents) on a solid surface may be selected and adapted for use on a droplet actuator. Digital microfluidic liquid handling protocols may be used for recovery of dried reagents. Liquid reagents (e.g., oil filler fluid, rehydration buffers, and certain assay reagents) may also be stored on a droplet actuator, and may coat the reagents prior to reconstitution. Reagents may be dried in a reservoir or fluid passage leading to a droplet operations gap or surface. Reagents may be dried on a droplet operations surface, such as a hydrophobic surface of a droplet actuator.

Reagents stored on a droplet actuator may be dried reagents, liquid reagents, and/or any combination thereof and are suitable for conducting one or more sample preparation protocols and/or one or more assay protocols. In one example, all reagents for conducting one or more sample preparation protocols and/or one or more assay protocols may be provided as dried reagents on a droplet actuator. In another example, a single reagent may be provided as a dried reagent and all other reagents may be provided as liquid reagents.

Sample preparation on a droplet actuator typically involves purifying a sample and/or lysing a sample to release molecular targets for one or more molecular assays. Sample preparation protocols that may be performed on a droplet actuator using one or more dried and reconstituted reagents and/or any combination of dried and liquid reagents may include, but are not limited to, blood preparation (e.g., agglutinating blood cells, agglutinating red blood cells, and lysing blood cells), and various lysing protocols for cells, spores, bacteria, fungi, virus, armored RNA, and armored DNA.

Molecular assays that may be performed on a droplet actuator using one or more dried and reconstituted reagents and/or any combination of dried and liquid reagents may include, but are not limited to, immunoassays, electrochemical assays, enzymatic assays, polymerase chain reaction (PCR) assays, and/or reverse transcriptase (RT)-PCR assays.

The invention provides methods for drying one or more assay reagents on a solid surface of a droplet actuator and for reconstituting the dried reagent(s). In one example, the methods of the invention may include, but are not limited to, the following steps:
1. Depositing an aqueous droplet(s) that contains one or more reagents on a surface of a droplet actuator;
2. Drying the droplet(s) to yield a dried composition on the surface of the droplet actuator;
3. Covering the dried composition with an oil filler fluid; and
4. Transporting a second aqueous droplet (i.e., rehydration droplet) in the oil filler fluid to contact the dried composition and thereby resuspend one or more dried reagents.

A droplet actuator may, for example, include a bottom substrate and a top substrate that are separated by a gap. The bottom substrate may include an electrode arrangement, such as a path and/or array of droplet operations electrodes (e.g., electrowetting electrodes) and one or more fluid reservoir electrodes that may be coated with a hydrophobic material (e.g., Cytop). The hydrophobic coating is provided for efficient electrowetting of droplets. The top substrate may include a single large ground reference electrode that may also be coated with a hydrophobic material. One or more droplets (e.g., sample droplets, reagent droplets) may be positioned in the gap between the two substrates. The gap between top and bottom substrates may be filled with a filler fluid, such as an oil filler fluid, to prevent evaporation of the droplets and to facilitate droplet operations. Examples of suitable oil filler fluids include silicone oil, perfluorinated oil, and hexadecane. The viscosity of the oil filler fluid may range from about 0.5 cSt to about 15 cSt. The oil filler fluid may, for example, be a silicone oil that has a viscosity ranging from about 1 cSt to about 10 cSt. In one example, the oil filler fluid may be 7 cSt silicone oil with 0.005% Span 85.

In one embodiment, reagent droplets may be loaded onto and dried onto electrodes on a droplet actuator. For example, reagent droplets may be deposited atop and dried onto certain droplet operations electrodes (e.g., electrowetting electrodes) of the droplet actuator. Droplet operations are conducted atop droplet operations electrodes on a droplet operations surface. In another example, reagent droplets may be deposited atop and dried onto one or more reservoir electrodes on the droplet actuator. In another embodiment, reagent solutions may be deposited onto a plastic surface of the droplet actuator. In another embodiment, reagent solutions may be deposited into a fluid passage of the droplet actuator leading to a droplet operations surface or gap. In another embodiment, reagent solutions may be deposited in a liquid reservoir of the droplet actuator, where the reservoir has a shape or feature designed to permit the liquid to settle and dry without flowing into and potentially clogging a fluid passage leading from the reservoir onto a droplet operations surface or into a droplet operations gap.

A reagent droplet may include one or more reagents. A reagent droplet may have a volume ranging from about 1 nanoliter (nL) to about 3 milliliters (mL) or from about 5 nL to about 1 mL. Reagent droplets may be dried directly on a surface of the droplet actuator or combined with reagent stabilization and/or protection compounds prior to drying on the surface. Examples of reagents may include, but are not limited to, beads, proteins, nucleic acids, salts, sugars, and/or surfactants. Specific examples of reagents may include, but are not limited to, an antibody, an antibody attached to a bead, a protease (e.g., protease K), a lectin (e.g., *Phaseoulus vulgaris* agglutinin), a virus, a spore, a bacteria, a fungus, an armored RNA, an armored DNA, a bacteriophage (e.g., MS2), a polymer (e.g., a temperature sensitive polymer), a fluorophore, a lysis reagent, a buffer (e.g., a wash buffer, an elution buffer), a surfactant, and/or a magnetically responsive bead.

A rehydration droplet may include a rehydration buffer and a surfactant for efficient reconstitution of dried reagent droplets. Examples of rehydration buffers include PBS with 0.1% Tween® 20, PBS with 0.02% Tween® 20, and water with 0.02% Tween® 20. Higher concentrations of surfactant (e.g., 0.1% Tween® 20) provide for more rapid reconstitution of dried reagent spots. In another example, a rehydration droplet may be a droplet of sample fluid to be analyzed. In various embodiments, the volume of a rehydration droplet may range from about 10 picoliters (pL) to about 10 mL or from about 100 pL to about 5 mL or from about 50 nL to about 2 mL or from about 100 nL to about 0.5 mL. In various embodiments, the ratio of a rehydration droplet volume to one electrode may range from about 1 pL:1 electrode to about 5 mL:1 electrode or from about 10 pL:1 electrode to about 3 mL:1 electrode or from about 1 nL:1 electrode to about 1 mL:1 electrode or from about 10 nL:1 electrode to about 0.5 mL:1 electrode or from about 50 nL:1 electrode to about 0.3 mL:1 electrode.

Liquid storage modules may be assembled onto a droplet actuator during manufacturing and used to store liquid reagents, such as oil filler fluid (e.g., 7 cSt oil with 0.005% Span 85) and rehydration buffers.

5.1.1 Dry Reagent Storage

Existing technologies for drying reagent fluids on a solid surface may be selected and adapted for use on a droplet actuator. In one example, a reagent drying technology may be selected for efficient recovery of dry reagents in an oil-filled droplet actuator. In another example, reagent stabilization and/or protection compounds may be selected such that they do not substantially interfere with the assay and/or droplet operations. In yet another example, a reagent drying technology may be selected for long term stability (shelf-life) at different environmental conditions (e.g., shipping temperatures, humidity, etc). In some cases, reagent droplets are so small that no special drying techniques are required. In yet another example, dispensing operations for reagent reconstitution may be automated such that user intervention is not required.

In one embodiment, the methods of the invention provide for drying reagent solution droplets directly on the surface of a droplet actuator without the addition of reagent stabilization and/or protection compounds. Examples of reagent solutions that may be dried directly on a surface and reconstituted via droplet operations using a rehydration droplet may include, but are not limited to, magnetically responsive bead solutions, wash buffers, lysis buffers, elution buffers, IgG (0.6-1.2 mg/mL), BSA (20 mg/mL), MS2 phage stock solutions (1:10 and 1:100 dilutions), and/or lectin solutions (200 μg/mL in PBS).

In another embodiment, the methods of the invention use one or more stabilizing agents in the aqueous reagent droplet for preservation and controlled release of dried assay reagents in a droplet actuator. In one example, the stabilizing agent may be a polymer. In another example, the stabilizing agent may be a sugar matrix. Examples of suitable sugars may include dextrans, sucroses, and/or trehaloses. Trehalose and dextran are two sugars commonly used to stabilize proteins (i.e., preserve enzymatic activity) in dried reagent preparations. Trehalose has also been shown to enhance reverse transcription (RT)-PCR reactions by reducing DNA secondary structures and DNA melting temperature by about 2-3° C. Trehalose also provides thermostability to enzymes at higher temperatures. Examples of reagent solutions that may be combined with a stabilizing agent (e.g., trehalose/dextran matrices) prior to drying on a droplet actuator and reconstituted via droplet operations using a rehydration droplet may include, but are not limited to, MS2 phage stock solution (1:10 and 1:100 dilutions), lectins (200 μg/mL in PBS) for sample preparation, and/or PCR master mix solutions that may include enzymes, salts, probes, primers, and/or deoxynucleotides.

An example of a generic protocol used to evaluate the use of sugar matrices in storing dried assay reagents on a droplet actuator included the following steps: An aliquot (e.g., about 0.6 μL to about 1.5 μL or greater) of each test solution was spotted onto a droplet operations electrode (storage electrode) on a Cytop coated bottom substrate of a droplet actuator. Test solutions included a trehalose/dextran matrix and rhodamine dye for visualization of the test spots. Examples of trehalose/dextran matrix compositions are shown in Table 1. The test solutions may also include one or more assay reagents (e.g., RT-PCR master mix, magnetically responsive beads, MS2). The bottom substrate was incubated in an oven at about 35-37° C. overnight to dry the test spots onto the bottom substrate surface. The following day, the droplet actuator was assembled and stored in a desiccator at ambient conditions until use. After a certain period of time, oil filler fluid and rehydration buffer (e.g., water or PBS) were loaded onto the droplet actuator. Dried reagent spots were rehydrated by electrowetting a droplet of rehydration buffer to the location of the dried reagent. An example of a reconstitution protocol is described in reference to FIG. 3.

TABLE 1

| Sugar matrices | | |
| --- | --- | --- |
| Sugar solution | Trehalose % (w/v)* | Dextran % (w/v)* |
| A | 40 | 0 |
| B | 20 | 0 |
| C | 10 | 0 |
| D | 40 | 20 |
| E | 20 | 10 |
| F | 0 | 0 |

*Final concentration after reconstitution

Parameters assessed in evaluating sugar matrices for dry reagent storage on a droplet actuator included reagent droplet volume, microfluidic transport (e.g., viscosity, inadvertent droplet splitting), and reconstitution time. The volume of reagent droplet that can be loaded on a droplet operations electrode is dependent on the composition of the trehalose/dextran sugar matrix. For example, greater than about 1.5 μL of reagent solution containing 40% trehalose/20% dextran may be larger than the typical gap height of a droplet actuator (i.e., 275 μm). To maintain droplet integrity after reconstitution of a dried reagent, the reconstituted droplet may be transported away from the storage electrode as a 2× droplet. Reconstituted droplets may be evaluated using an appropriate digital microfluidic assay protocol and/or removed from the droplet actuator and evaluated using an appropriate on-bench protocol.

In one example, RT-PCR master mix was combined with sugar matrices and evaluated for reconstitution and electrowetting on a droplet actuator as described in reference to Table 1. Two RT-PCR stock solutions containing different concentrations of enzyme and master mix were used. One RT-PCR stock solution included 10× enzyme and 5× master mix with very little glycerol and the second RT-PCR stock solution included 2.3× enzyme and 2.3× master mix with glycerol. Dilutions of the 10× enzyme/5× master mix stock solution are shown in Table 2. Aliquots of stock solution and dilutions were combined with aliquots of the sugar matrices shown in Table 1. A 0.6 μL aliquot of each combined solution was spotted onto individual droplet operations electrodes of a droplet actuator as described in reference to Table 1 and rehydrated using an electrode pulsing protocol described in reference to FIG. 3. Over 180 droplets of dried RT-PCR master mix/sugar matrix solutions were assessed. All dried droplets were reconstituted in about 3 minutes or less. Each type of dried master mix solution was reconstituted in approximately similar time frames based on sugar content as shown in Table 3.

TABLE 2

| RT-PCR master mix dilutions | |
| --- | --- |
| Master mix solution | |
| 1 | 6× enzyme |
| | 3× master mix (no glycerol) |
| 2 | 2.73× enzyme |
| | 1.365× master mix (no glycerol) |
| 3 | 1.365× enzyme |
| | 0.6825× master mix (no glycerol) |
| 4 | 1.365× enzyme |
| | 1.365× master mix (glycerol) |

*Final concentration after reconstitution

TABLE 3

| Sugar matrices | | | |
| --- | --- | --- | --- |
| Sugar solution | Trehalose % (w/v)* | Dextran % (w/v)* | Pulses (seconds) |
| A | 40 | 0 | ~50 |
| B | 20 | 0 | ~50 |
| C | 10 | 0 | ~40 |
| D | 40 | 20 | ~150 |
| E | 20 | 10 | ~125 |
| F | 0 | 0 | ~50 |

Figure 1:
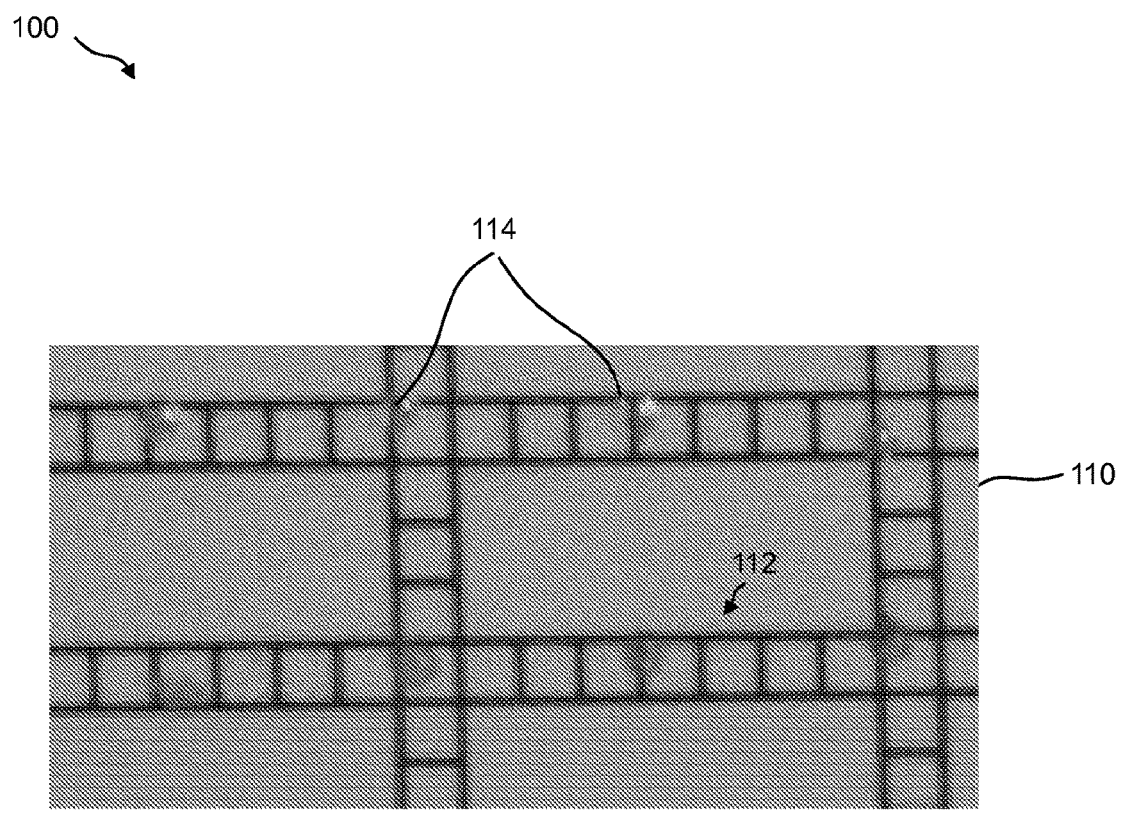
FIG. 1 illustrates a top view of an example of a portion of a droplet actuator and also shows an example of an array of reagent droplets dried on certain droplet operations electrodes.

FIG. 1 illustrates a top view of a portion of a droplet actuator 100 and also shows an example of an array of reagent droplets dried on certain droplet operations electrodes. In this example, the reagent droplets were loaded onto a droplet actuator and dried as described in reference to Table 1. Droplet actuator 100 may include a bottom substrate 110 and a top substrate (not shown) that are separated by a gap. The gap may be filled with a filler fluid, such as silicone oil (not shown). Bottom substrate 110 may, for example, be a printed circuit board (PCB). An arrangement, such as a path and/or array of droplet operations electrodes 112 (e.g., electrowetting electrodes) may be formed as a part of the bottom substrate 110, and arranged to conduct droplet operations in the droplet operations gap. Droplet operations are generally conducted atop droplet operations electrodes 112 in the droplet operations gap. One or more reagent solution droplets 114 may be loaded onto certain droplet operations electrodes 112 (storage electrodes) and dried for storage. Reagent solution droplets 114 may, for example, be from about 0.6 µL to about 1 µL in volume. As reagent solution droplets 114 were dried, they became localized between adjacent electrodes. This effect is likely due to the topography of droplet operations electrodes 112. Divots, patterned surfaces, hydrophilic regions, or other features may be used to localize dried reagents directly atop electrodes; however, localization of the dried reagent droplets between electrodes does not appear to affect reconstitution of the dried reagent droplet.

Figure 2:
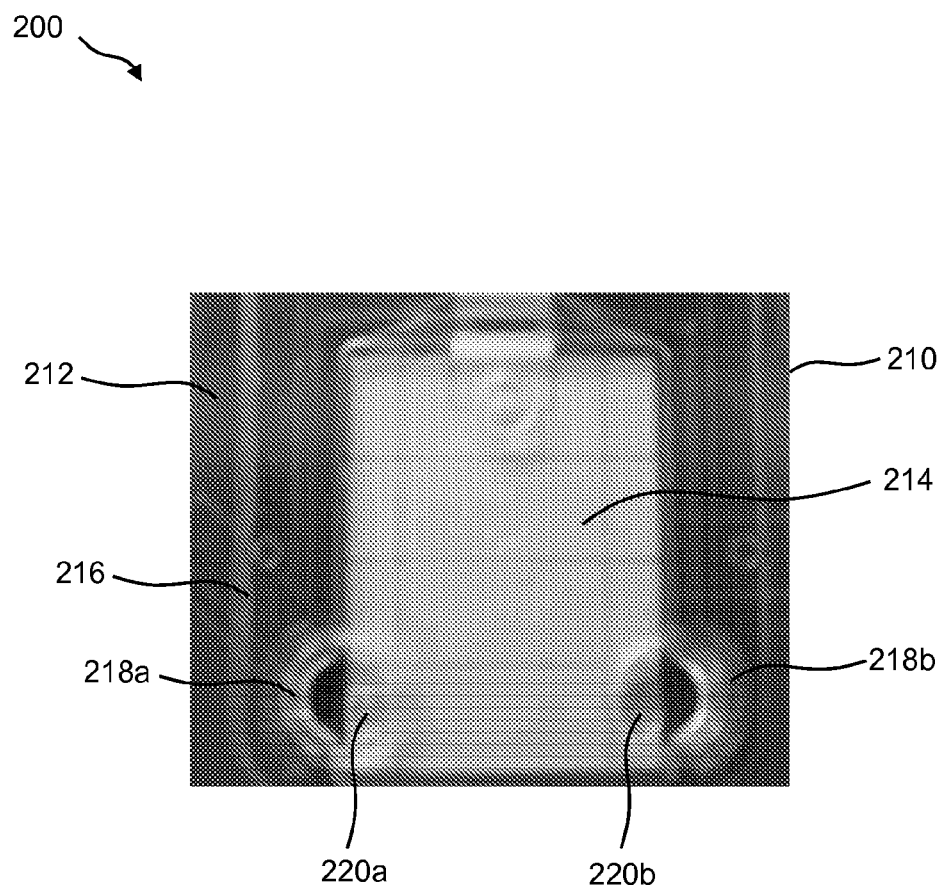
FIG. 2 illustrates a top view of an example of a portion of a droplet actuator and also shows an example of dried reagent droplets on an on-actuator reagent dispensing electrode.

Loading and drying a reagent solution droplet onto an on-actuator reservoir was also evaluated. FIG. 2 illustrates a top view of a portion of a droplet actuator 200 and also shows an example of dried reagent droplets on an on-actuator reagent dispensing electrode. Droplet actuator 200 may include a bottom substrate 210 and a top substrate 212 that are separated by a gap. The gap may be filled with a filler fluid, such as silicone oil (not shown). Bottom substrate 210 may, for example, be a PCB. Bottom substrate 210 may include a reagent dispensing electrode 214. Reagent dispensing electrode 214 may be segmented into multiple individually controlled electrodes. The combined features of bottom substrate 210 and top substrate 212 form an on-actuator reagent reservoir 216. On-actuator reagent reservoir 216 has, for example two input ports 218 (e.g., input ports 218a and 218b). Therefore, input ports 218a and 218b are integrated into top substrate 112 in proximity to at least a portion of reagent dispensing electrode 214. A port (e.g., input ports 218a and 218b) provides an entrance/exit (opening) to the droplet operations gap. Liquid may flow through the port into any portion of the gap, e.g., into a reservoir region of the gap or onto a droplet operations pathway. A port may be used to fill the gap with filler fluid. However, in most cases, a reagent fluid or sample fluid flowing through a port should come into sufficient proximity with an electrode, such that the electrode can be used to conduct one or more droplet operations using the liquid, such as droplet transport, splitting, and/or dispensing.

On-actuator reagent reservoir 216 and input ports 218a and 218b are designed such that the dried reagent droplet is accessible to electrowetting for rehydration. One or more reagent solution droplets 220 may be loaded onto reagent dispensing electrode 214 and dried for storage. For example, a reagent solution droplet 220a may be loaded via input port 218a onto reagent dispensing electrode 214 and dried for storage. Further, a reagent solution droplet 220b may be loaded via input port 218b onto reagent dispensing electrode 214 and dried for storage. Reagent solution droplets 220 may, for example, be about 20 µL in volume.

5.1.2 Reagent Reconstitution Protocols

The reagent reconstitution methods of the invention use digital microfluidic liquid handling protocols for recovery of dried reagents. In one embodiment, the methods of the invention use electrowetting mediated droplet operations for manipulating an aqueous droplet for recovery of a dried reagent droplet. Importantly, the inventors have discovered that the dried reagents can be coated with an oil filler fluid and substantially fully reconstituted by transporting a droplet through the oil and into contact with the dried reagent.

Droplet voltages in electrowetting mediated droplet operations may, for example, range from about 0.5 volts to about 1000 volts; or from about 2 volts to about 700 volts; or from about 4 volts to about 500 volts. Electrowetting mediated droplet operations use AC voltage with frequencies ranging, for example, from about 0.1 Hz to about 10000 Hz; or from about 1 Hz to about 1000 Hz; or from about 2 Hz to about 500 Hz. In another embodiment, the methods of the invention use dielectrophoresis mediated droplet operations.

The reagent reconstitution methods of the invention provide for recovery of greater than about 50% of the dried reagent droplet; or greater than about 80% of the dried reagent droplet; or greater than about 90% of the dried reagent droplet; or greater than about 95% of the dried reagent droplet; or greater than about 99% of the dried reagent droplet.

The reagent reconstitution methods of the invention provide for reconstitution (recovery) of substantially all of a dried reagent droplet in less than about 15 minutes; or less than about 7 minutes; or less than about 5 minutes; or less than about 3 minutes.

In a preferred embodiment, an electrode pulsing protocol (i.e., electrowetting mediated droplet pulsing) may be used to manipulate an aqueous droplet for reconstitution of a dried reagent droplet. In various embodiments, the pulsing may have an ON/OFF pulsing ratio from about 1:1 to about 20:1; or from about 5:1 to about 15:1; or from about 8:1 to 12:1. In various embodiments, the electrowetting mediated pulsing may have an ON/OFF pulsing ratio from about 1:1 to about 20:1 wherein each pulsing cycle is from about 1 nanosecond to 1 minute; or from about 1 millisecond to about 30 seconds; or from about 100 milliseconds to about 5 seconds.

FIGS. 3A, 3B, and 3C illustrate top views of an example of a portion of an electrode arrangement 300 of a droplet actuator and show a process of performing a reagent reconstitution protocol on a droplet actuator. The method of the invention of FIGS. 3A through 3C is an example of a reagent reconstitution protocol in which electrode pulsing is used to reconstitute a dried reagent stored on a certain droplet operations electrode on a droplet actuator.

Electrode arrangement 300 may include a path and/or array of droplet operations electrodes 310 (e.g., electrowetting electrodes) that is configured to conduct droplet operations. Droplet operations are conducted atop droplet operations electrodes 310 on a droplet operations surface. A dried concentrated reagent droplet 312 may be present at a certain droplet operations electrode 310. In one example, dried reagent 312 may be a reverse transcription-polymerase chain reaction (RT-PCR) master mix droplet that includes enzyme, salts, primer pairs, deoxynucleotides, and probes that are sufficient for RT-PCR amplification. Dried reagent 312 may, for example, be dried in place by manual spotting or by an automated printing device. An example of a process of reconstituting dried assay reagents using electrode pulsing may include, but is not limited to, the following steps. Reagent droplet 312 may be coated with a filler fluid, such as an oil filler fluid, such as a silicone oil filler fluid.

In one step and referring to FIG. 3A, a dried reagent 312 is present at a certain droplet operations electrode 310 and is ready for reconstitution. An oil filler fluid (not shown) coats the surface including the dried reagent 312. Dried reagent 312 provides a high concentration of dried regent. A rehydration droplet 314 is present at another droplet operations electrode 310 and is ready to be transported via droplet operations toward dried reagent 312. Rehydration droplet 314 may be a 1× droplet, meaning that its footprint is approximately equal to the area of one droplet operations electrode 310. In one example, rehydration droplet 314 may be a rehydration buffer (e.g., water with 0.02% Tween® 20) that is used to reconstitute a dried reagent droplet prior to mixing and incubation with a sample droplet (not shown). In another example, rehydration droplet 314 may be a sample droplet that is used to reconstitute dried reagent 312.

In another step and referring to FIG. 3B, an incubation process is provided in which rehydration droplet 314 is transported using droplet operations along droplet operations electrodes 310 and into contact with dried reagent 312. In doing so, dried reagent 312 is rehydrated to form a reaction droplet 316. To facilitate rehydration of reagent droplet 312, the droplet operations electrode 310 holding reagent droplet 312 may be repeatedly pulsed ON and OFF. For example, the droplet operations electrode 310 may be pulsed ON for about 0.9 seconds (e.g., 300 V, 30 Hz) and OFF for about 0.1 second. The pulsing may be repeated from about 40 to about 150 times. Increased time with the droplet operations electrode 310 ON provides for more efficient wetting of the electrode and increases the time the rehydration droplet has to resuspend the dried reagent. Pulsing also introduces convection within the droplet which further facilitates rehydration of a dried reagent droplet. In an alternative embodiment, the dried reagent may be provided in a conventional hydrophobic microfluidic channel, and an electrode positioned adjacent the channel may be used to pulse a droplet in the channel (surrounded by an oil filler fluid) in the presence of a dried reagent on a surface of the channel to cause the reagent to be reconstituted in the channel.

In another step and referring to FIG. 3C, after an incubation period sufficient to reconstitute the dried reagent (e.g., 3 minutes or less), reaction droplet 316 is transported using droplet operations along droplet operations electrodes 310 for further processing. Additionally, reaction droplet 316 is transported as a 2× droplet, meaning that its footprint is approximately 2 times the area of one droplet operations electrode 310. Transport of reaction droplet 316 as a 2× droplet prevents inadvertent droplet splitting.

In another embodiment, a droplet shuttling protocol (i.e., electrowetting mediated droplet shuttling) may be used to manipulate an aqueous droplet for reconstitution of a dried reagent droplet. In one example, an aqueous droplet may be shuttled across a dried reagent droplet by turning ON two adjacent droplet operations electrodes. In another example, an aqueous droplet may be shuttled across a dried reagent droplet by turning ON one adjacent droplet operations electrode. The frequency of droplet shuttling across a dried reagent droplet may, for example, range from about once every 10 milliseconds to about once every 20 seconds; or from about once every 100 milliseconds to about once every 15 seconds; or from about once every 200 milliseconds to about once every 10 seconds.

FIGS. 4A through 4E illustrate top views of electrode arrangement 300 of FIG. 3A and show another process of performing a reagent reconstitution protocol on a droplet actuator. The method of the invention of FIGS. 4A through 4E is an example of a reagent reconstitution protocol in which shuttling an aqueous droplet back and forth is used to reconstitute a dried reagent droplet stored on a certain droplet operations electrode on a droplet actuator. An example of a process of reconstituting dried assay reagents using droplet shuttling may include, but is not limited to, the following steps.

Figure 4A:
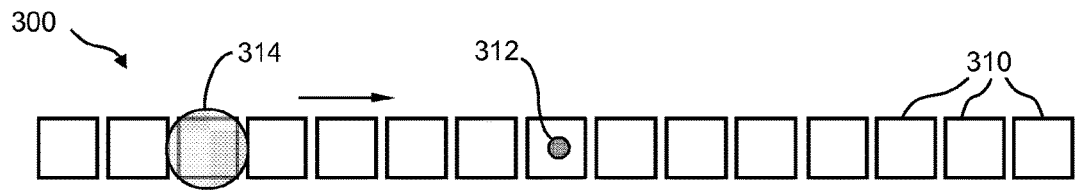

In one step and referring to FIG. 4A, a dried reagent 312 is present at a certain droplet operations electrode 310 and is ready for reconstitution. Dried reagent 312 provides a high concentration of dried regent. A rehydration droplet 314 is present at another droplet operations electrode 310 and is ready to be transported via droplet operations toward dried reagent 312. Rehydration droplet 314 may be a 1× droplet.

Figure 4B:
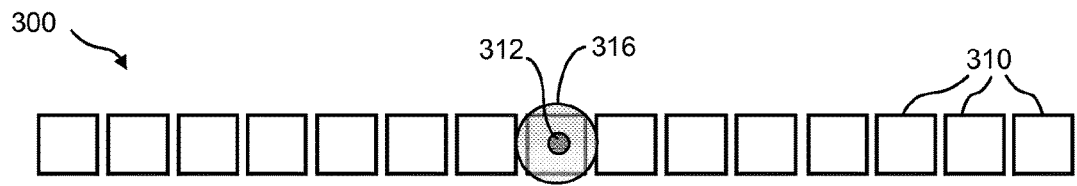

In another step and referring to FIG. 4B, rehydration droplet 314 is transported using droplet operations along droplet operations electrodes 310 and into contact with dried reagent 312. In doing so, dried reagent 312 is rehydrated to form a reaction droplet 316.

Figure 4C:
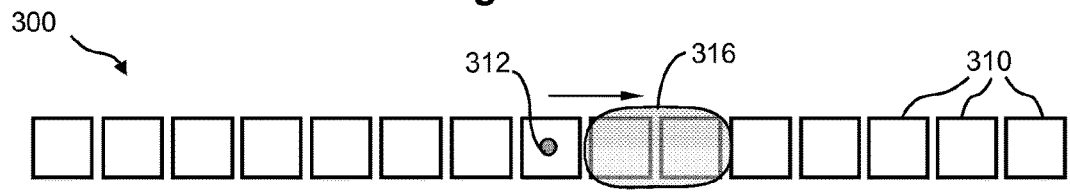
Figure 4D:
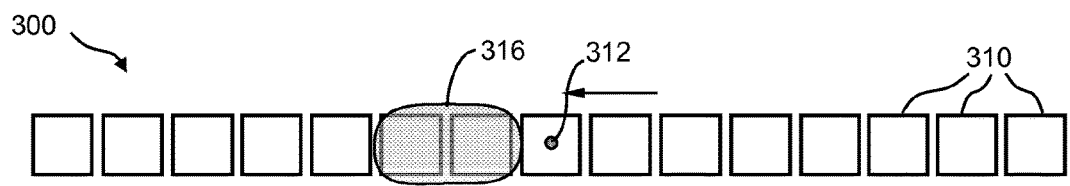
Figure 4E:
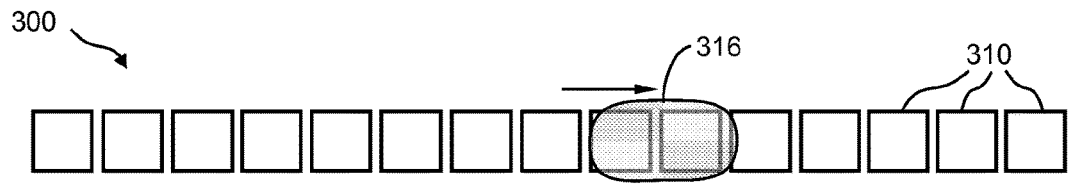

In other steps and referring to FIGS. 4C, 4D, and 4E, a process is provided of shuttling reaction droplet 316 back and forth over the droplet operations electrode 310 holding the dried reagent 312 in order to fully rehydrate dried reagent 312. Reaction droplet 316 is shuttled as a 2× droplet by turning ON the two droplet operations electrodes 310 adjacent to dried reagent 312. Transport of reaction droplet 316 as a 2× droplet prevents inadvertent droplet splitting. As reaction droplet 316 is shuttled back and forth over the droplet operations electrode 310 holding the dried reagent 312, dried reagent 312 is rehydrated. The shuttling process may be repeated any number of times sufficient for rehydration of dried reagent 312. Reaction droplet 316 is now ready for further processing.

5.1.3 Liquid Reagent Storage

Reconstitution buffers as well as certain other reagents may be stored in a liquid form on a droplet actuator. One or more physical structures and/or features may be incorporated into the droplet actuator and used for containment of the liquid reagents. In one example, the physical structures and/or features may be selected to provide containment of liquid reagents during shipment. Large volumes of reagent fluids, such as wash buffers, may be stored in separate reservoirs (e.g., reservoirs atop the top substrate). Reagents suitable for liquid storage may be selected based on shelf-life studies.

Liquid reagents preloaded and stored on a droplet actuator may be surrounded by a protective layer so that they are contained until the droplet actuator is used. For example, the protective layer may be a frangible layer (pressure sensitive) such that insertion of the droplet actuator into the instrument actuates breakage of the protective layer. As the protective layer is broken, liquid reagents may, for example, be released into proximity of certain droplet operations electrodes where they may be dispensed by droplet operations. In another example, liquid reagents may be released into one or more adjacent compartments in which dried reagents are stored. As the liquid enters the compartment the dried reagent is reconstituted (i.e., rehydrated).

5.2 Example Application

The methods of the invention are used to provide a point-of-care (POC) diagnostic device for integrated (i.e., sample-to-answer) sample preparation and multiplexed detection of HIV. In this example, dried reagents for sample preparation, immunoassays for antibodies to HIV, and RT-PCR for determination of HIV viral load may be stored on a droplet actuator. Liquid reagents, e.g., wash buffers and oil filler fluid may also be stored on the droplet actuator.

5.3 Systems

It will be appreciated that various aspects of the invention may be embodied as a method, system, computer readable medium, and/or computer program product. Aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the invention may be written in an object oriented programming language such as Java, Smalltalk, C++ or the like. However, the program code for carrying out operations of the invention may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The invention may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The invention may be applied to any wireless/wireline communications network, regardless of physical componentry, physical configuration, or communications standard(s).

Certain aspects of invention are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the invention.

6 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

We claim:

1. A method of providing a droplet comprising one or more reagents, the method comprising:
    (a) depositing a first aqueous droplet comprising the one or more reagents on a surface;
    (b) drying the first aqueous droplet to yield a dried composition on the surface comprising the one or more reagents;
    (c) covering the dried composition with oil; and
    (d) causing a second aqueous droplet in the oil to contact the dried composition by pulsing or shuttling the second aqueous droplet and thereby resuspending one or more reagents.

2. The method of claim 1, wherein the first aqueous droplet further comprises a stabilizing agent.

3. The method of claim 2, wherein the stabilizing agent comprises a sugar.

4. The method of claim 3, wherein the sugar is selected from a group consisting of: dextrans, sucroses, and trehaloses.

5. The method of claim 2, wherein the stabilizing agent comprises a polymer.

6. The method of claim 2, wherein the one or more reagents comprise a reagent selected from a group consisting of: beads, proteins, nucleic acids, salts, sugars, and surfactants.

7. The method of claim 1, wherein the one or more reagents comprise reagents selected for amplifying a target nucleic acid when combined with a sample comprising the target nucleic acid.

8. The method of claim 1, wherein the one or more reagents comprises an antibody.

9. The method of claim 1, wherein the one or more reagents comprises an antibody attached to a bead.

10. The method of claim 1, wherein the one or more reagents comprises a protease.

11. The method of claim 1, wherein the one or more reagents comprises protease K.

12. The method of claim 1, wherein the one or more reagents comprises a lectin.

13. The method of claim 1, wherein the one or more reagents comprises a *phaseoulus vulgaris* agglutinin.

14. The method of claim 1, wherein the one or more reagents comprises a bead.

15. The method of claim 1, wherein the one or more reagents comprises a virus.

16. The method of claim 1, wherein the one or more reagents comprises a spore.

17. The method of claim 1, wherein the one or more reagents comprises a bacteria.

18. The method of claim 1, wherein the one or more reagents comprises a fungus.

19. The method of claim 1, wherein the one or more reagents comprises an armored RNA.

20. The method of claim 1, wherein the one or more reagents comprises an armored DNA.

21. The method of claim 1, wherein the one or more reagents comprises a bacteriophage.

22. The method of claim 1, wherein the one or more reagents comprises MS2.

23. The method of claim 1, wherein the one or more reagents comprises a polymer.

24. The method of claim 1, wherein the one or more reagents comprises a temperature sensitive polymer.

25. The method of claim 1, wherein the one or more reagents comprises a fluorophore.

26. The method of claim 1, wherein the one or more reagents comprises a nucleic acid.

27. The method of claim 1, wherein the one or more reagents comprises a lysis reagent.

28. The method of claim 1, wherein the one or more reagents comprises a buffer.

29. The method of claim 1, wherein the one or more reagents comprises a magnetically responsive bead.

30. The method of claim 1, wherein the second aqueous droplet has a volume ranging from 10 picoliters to 10 milliliters.

31. The method of claim 1, wherein the first aqueous droplet has a volume ranging from one nanoliter to 3 milliliters.

32. The method of claim 1, wherein the first aqueous droplet has a volume ranging from five nanoliters to one milliliter.

33. The method of claim 1, wherein the second aqueous droplet has a volume ranging from 10 picoliters to 10 milliliters.

34. The method of claim 1, wherein the second aqueous droplet has a volume ranging from 100 picoliters to 5 milliliters.

35. The method of claim 1, wherein the second aqueous droplet has a volume ranging from 50 nanoliters to 2 milliliters.

36. The method of claim 1, wherein the second aqueous droplet has a volume ranging from 100 nanoliters to 0.5 milliliters.

37. The method of claim 1, wherein the first aqueous droplet comprises a surfactant.

38. The method of claim 1, wherein the second aqueous droplet comprises a surfactant.

39. The method of claim 1, wherein the surface comprises an electrode.

40. The method of claim 1, wherein the surface comprises a plastic surface.

41. The method of claim 1, wherein the surface is hydrophobic.

42. The method of claim 1, wherein the surface comprises an electrode and the dried composition is positioned on the electrode.

43. The method of claim 42, wherein the electrode is a component of an array of electrodes.

44. The method of claim 43, wherein the array of electrodes is configured to conduct droplet operations on the surface.

* * * * *